United States Patent [19]

Rhoades

[11] 4,221,571
[45] Sep. 9, 1980

[54] SOLAR HEATED ANAEROBIC DIGESTOR

[76] Inventor: Don Rhoades, Box 312, High Level, Alberta, Canada

[21] Appl. No.: 959,669

[22] Filed: Nov. 13, 1978

[51] Int. Cl.³ .................. C10J 3/20; C05F 11/08; B01J 19/00; F24J 3/02

[52] U.S. Cl. .................................. 48/111; 34/93; 71/10; 210/12; 210/180; 210/605; 422/184; 422/200; 422/231; 422/234

[58] Field of Search ............... 34/93; 126/271, 270, 126/417, 418, 451; 422/184, 200, 231, 234; 210/2, 12, 180, 187; 71/9, 10; 48/111

[56] References Cited

U.S. PATENT DOCUMENTS

| 430,762 | 6/1890 | Taylor | 34/93 X |
| 2,638,444 | 5/1963 | Kappe | 210/12 X |
| 2,857,634 | 10/1958 | Garbade et al. | 126/270 X |
| 3,933,628 | 1/1976 | Varani | 126/271 X |
| 3,969,829 | 7/1976 | Alban | 34/93 |
| 4,057,401 | 11/1977 | Boblitz | 126/270 X |

Primary Examiner—Michael S. Marcus
Attorney, Agent, or Firm—E. P. Johnson

[57] ABSTRACT

A solar heated anaerobic digestor is provided, adapted to utilize organic material capable of decomposing to produce methane gas and a liquid fertilizer. The sealed anaerobic digestor is wrapped with a layer of heat absorptive material followed by a series of abutting removable panels of insulative material. Insulative panels may be temporarily removed to expose the heat absorptive material to solar radiation and may be replaced when the solar radiation diminishes. A layer of transparent material wrapped in outwardly spaced relation around the insulatng panels is capable of transmitting solar radiation while providing protection against environmental elements. Additional heating means extending into the digestor provide auxiliary heat as required.

3 Claims, 4 Drawing Figures

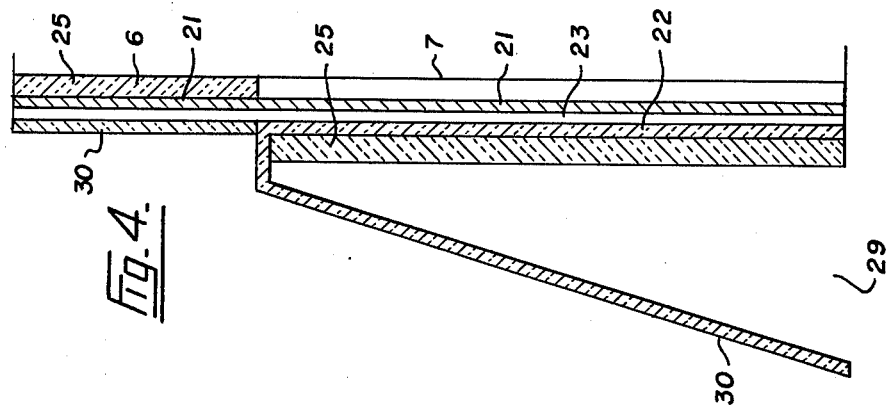
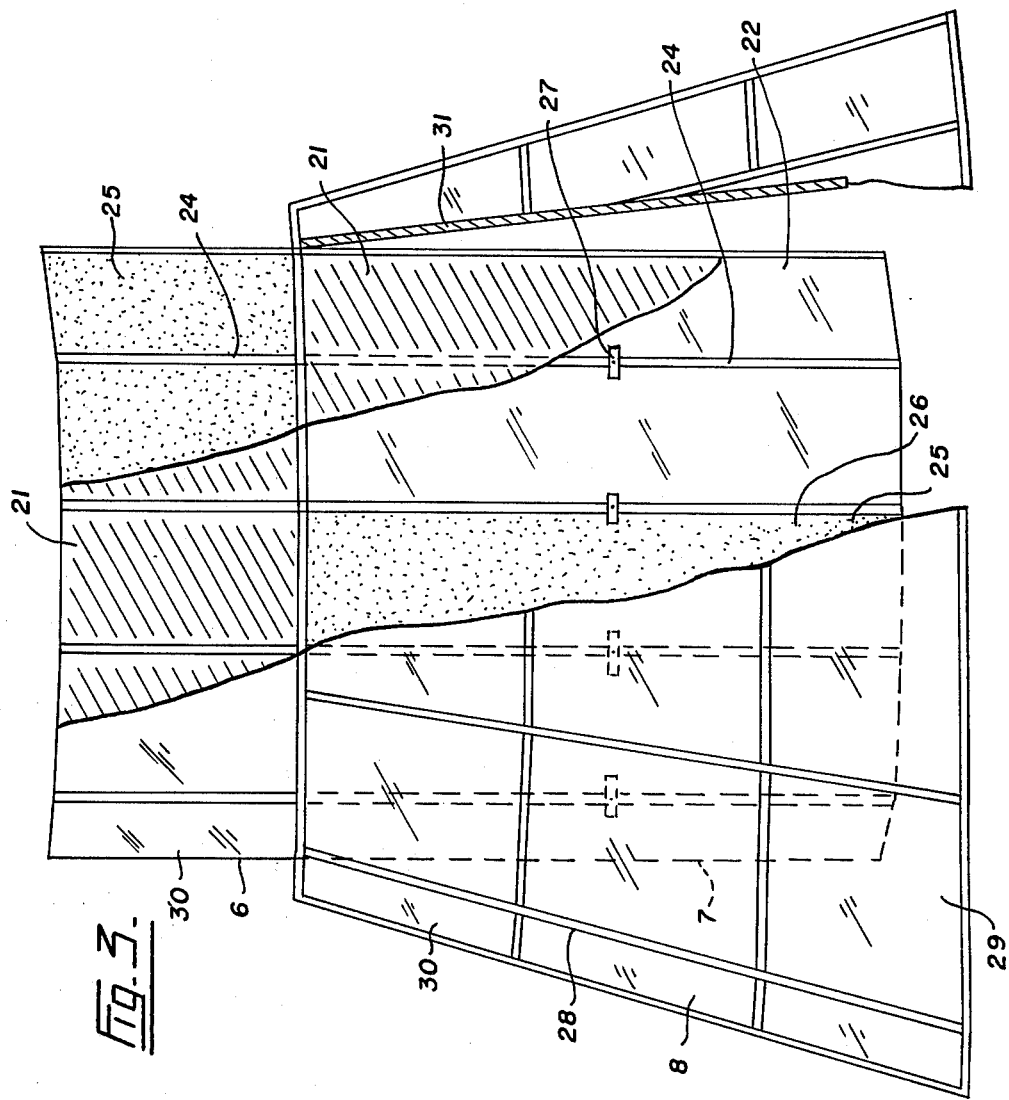

SOLAR HEATED ANAEROBIC DIGESTOR

BACKGROUND OF THE INVENTION

The present invention relates to an anaerobic digestor which decomposes organic material to produce a liquid fertilizer and methane gas, and in particular to an anaerobic digestor heated by solar energy.

It is well known to produce methane gas through the anaerobic decomposition of organic material or wastes containing methanogenic bacteria. The usual process is to combine the organic materials in a sealed container in which is maintained an anaerobic atmosphere and a constant temperature in the range of 90–95° F. A period of approximately 30 days is required for an initial incubation before a sufficient quantity of gas withdrawn. A continuous process can be established whereby the feedstock of organic material is continually fed into the tank, and the expired effluent, a liquid fertilizer, is continually removed from the tank. The gas collected can be compressed and used as a methane energy source.

A problem inherent in the process exists in keeping the temperature at a constant value in the range of 90–95° F., as required for the growth of the methanogenic bacteria. In mild climates some of the methane gas produced by the process can be used to heat the digestor, however in colder climates this is not efficient since a large proportion of the methane is used in the heating, leaving a low net yield of methane. Solar energy can be used to supplement the gas heating of the digestor in order to maintain an efficient operation.

Verani, in U.S. Pat. No. 3,933,328 describes an anaerobic digestor which is solar heated. The digestor is buried in the ground and covered with a liquid filled pond. The liquid, being absorptive of solar energy, is circulated through the digestor to heat the contents. A translucent roof, in the form of a dome or inflated bubble exterior of the pond, is used to establish a regulatory temperature environment.

Boblitz, in U.S. PAT. No. 4,057,401, provides a solar heated digestor which comprises a series of sealed containers surrounded with crushed stones, enclosed in a large chamber. The roof over the chamber is pivotal to be inclined at an angle to receive the sun's rays. A black wire screen covered with transparent material is positioned in the roof to absorb the solar energy, thereby heating the air in the roof which in turn is circulated around the sealed tanks.

The structures of Verani and Boblitz, although presumably efficient in using the solar radiation during the sunlight hours to heat the digestors, do not provide adequate restriction to heat loss to the outside environment during the non-sunlight hours, which in cold climates would allow the temperature within the digestor to fluctuate considerably.

SUMMARY OF THE INVENTION

In accordance with the invention there is provided a solar heated anaerobic digestor adapted to utilize a slurry of organic material capable of decomposing to produce a liquid fertilizer and methane gas, comprising: sealed digestor container means having adjoining upper and lower portions defined by upper and lower side wall segments, the lower portion of which is operative to contain the organic material and the upper portion of which is capable of containing the gas produced; means for introducing the slurry into the container means; means for draining slurry product from the container means; means in the upper portion for withdrawing gas produced; means in the lower portion for stirring the slurry; secondary heating means for heating the slurry present in the lower portion; a layer of heat absorptive material wrapped around the lower side wall segment; a plurality of abutting removable panels of insulative material enclosing the layer of heat absorptive material; a layer of insulative material wrapped around the upper side wall segment of the container means; a layer of transparent material wrapped around the panels and the upper side wall insulative material, said layer of transparent material being spaced outwardly from the insulating panels, whereby some of the panels may be temporarily removed to permit solar radiation to heat an exposed portion of the heat absorptive material, and may be replaced when the solar radiation diminishes, thereby enabling a combination of solar heat and heat obtained from the secondary heating means to be used to maintain the temperature of the contained slurry at a desirable level.

In winter daytime hours, those insulating panels facing the sun may be selectively removed, to permit solar radiation to be absorbed by the container contents. The panels are replaced after passage of the sun to reduce heat loss. By combining this feature with auxiliary heating of the container contents by way of burning some of the produced methane, a productive process is realized.

DESCRIPTION OF THE DRAWINGS

FIG. 3 is as FIG. 2 showing panels of the insulative material removed and having additional portions removed to view the underlying material.

FIG. 4 is a sectional view of the solar heated structure showing the layers of heat absorptive, insulative and transparent materials.

DESCRIPTION OF THE PREFERRED EMBODIMENT

Figure 1:
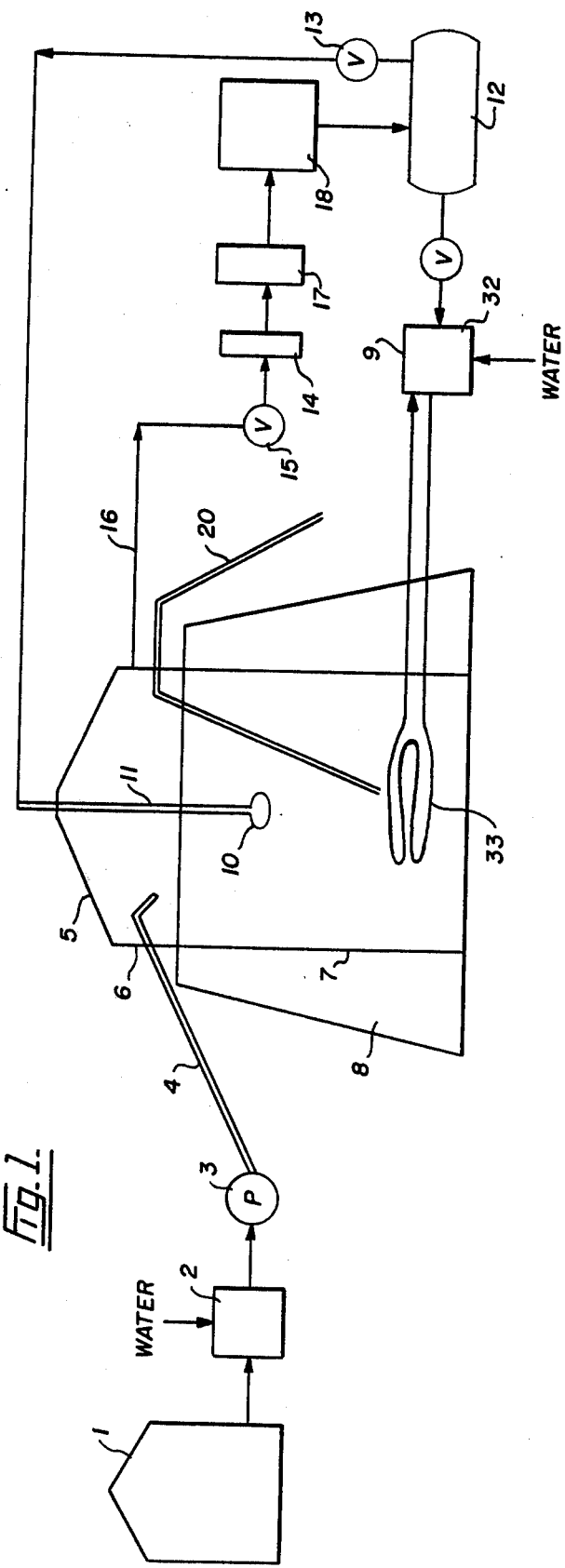
FIG. 1 is a schematic diagram of a typical farm scale operation utilizing the solar heated anaerobic digestor shown in cross-section.

The present invention finds application in the typical farm scale operation depicted in FIG. 1 wherein organic waste is anaerobically decomposed to produce a low grade methane gas suitable for use in heating farm buildings, while the liquid fertilizer remaining after the decomposition can be used as a plant nutrient source.

With reference to FIG. 1, organic material collected from the barn 1 is combined with water in a mixer 2 to form a slurry containing approximately 7% solids. A slurry of this water composition is necessary both to enable the slurry to be pumped and to provide a suitable medium for bacterial growth. A conventional water pump 3 is used to pump the slurry through influent tubing 4 to a sealed container 5. The sealed container 5 is composed of a closed cylindrical steel tank having an upper portion 6 defined by the lower side wall segment adjoining a lower portion 7 defined by the lower side wall segment, the lower portion 7 being operative to contain slurry of organic material, and the upper portion 6 being left empty for the accumulation of the gases produced.

The organic material within the sealed container is initially allowed to digest or decompose for an incubation period of about 30 days before a sufficient quantity of gas is produced to be drawn off. The conditions essential for the decomposition include an anaerobic atmosphere, as provided by the sealed container 5, and a near constant temperature in the range of 90°–95° F., as provided by the solar heated structure 8 and the secondary gas heating means 9 which will be described later. During the decomposition, the slurry of organic material can be stirred to prevent a hard scum for forming on the surface of the slurry. A gas bubbler is used comprising a perforated hollow ring 10 submerged within the slurry and attached to hollow tubing 11 extending to a gas source such as the gas storage tank 12. A gas valve 13 inserted in the hollow tubing 11 is used to regulate the flow rate of the gas entering the container. Preferably methane gas is bubbled through the slurry; being the major gas produced during the decomposition, it is thus available and known not to alter the conditions for the decomposition.

When a sufficient quantity of gas has been produced, as indicated by a gas manometer 14, the gas is drawn off by opening gas valve 15 in the tubing 16 leading from the upper portion 6 of the sealed container. The water is removed from the gas in a water knock-out apparatus 17 prior to passing the gas through compressor 18 and into storage tank 12.

Effluent tubing 20 leads from the sealed container allowing the expired slurry product remaining in the tank to be drawn off for use as a liquid fertilizer. The effluent tubing 20 enters the upper portion 6 of the sealed container 5 and then assumes a downward incline into the slurry. In this manner the slurry is self-draining from the sealed container 5 lending the process to a continuous operation. The gas which accumulates in the upper portion 6 of the sealed container exerts a downward pressure on the slurry causing the slurry to be continually drained from the tank through the effluent tubing 20. Additional slurry can be pumped into the container through the influent tubing 4. If otherwise desired, a batch process can be assumed, draining and refilling the sealed container 5 with the use of the pump 3 at 30 day intervals.

Figure 2:
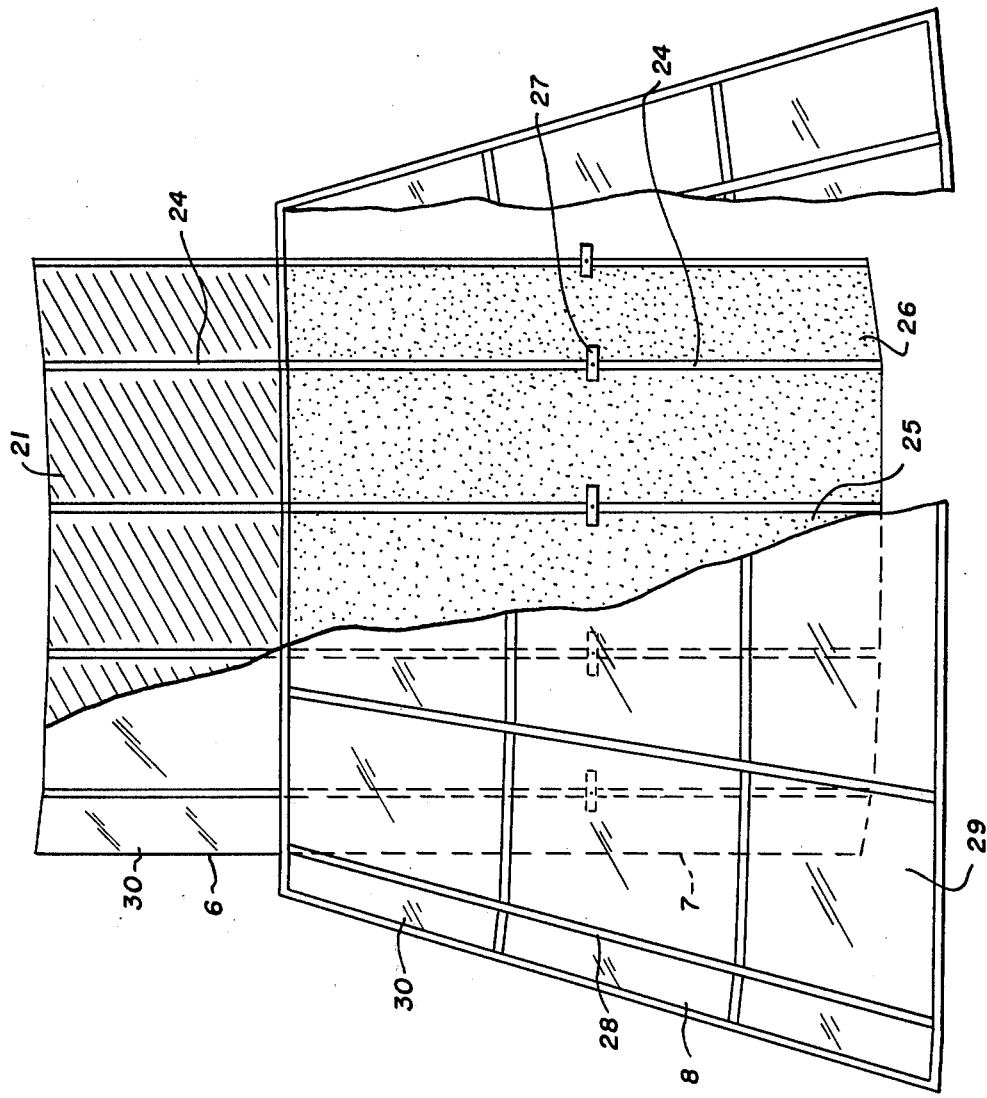
FIG. 2 is a perspective view of the anaerobic digestor enclosed within the solar heated structure, with a portion of the outer transparent material removed to view the inner area.

As previously discussed, it is necessary to maintain the temperature inside the sealed container 5 at a constant value in the range of 90°–95° F. in order to keep the decomposition operative. A solar heated structure 8 is provided exterior the sealed container 5. With reference to FIGS. 2, 3 and 4, a layer of heat absorptive material 21 is first wrapped around the lower side wall segment 7 of the sealed container 5. Black plastic material is suitable for this purpose, being absorptive of the energy associated with solar radiation. A first layer of transparent material 22 such as clear plastic capable of transmitting solar energy is wrapped over the black plastic. An air space 23 is left between these two layers by placing intermediate these two layers a first frame 24 of vertical wood slats at spaced intervals around the circumference of the upper side wall segment lower side wall segment 7 of the sealed container 5, and attaching the heat absorptive material 21 and the transparent material 22 to the first frame 24. Insulative material 25 is placed over the transparent material 22. Foam insulation having an R factor of 3.7 per inch has been found effective for the purposes of the present invention. The insulative material 25 is cut into panels 26 of size such that they fit within the spaced intervals of the first frame 24 and enclose the lower portion 7 of the sealed container 5. Clips 27 attached to the first frame 24 hold the panels 25 in place, such that the panels may be removed when desired.

On the upper side wall segment 6 of the sealed container 5, the insulative material 25 is permanently attached to the first frame 24 and further wrapped with the heat absorptive material 21 also attached to the first frame 24. It is desirable to maintain the temperature in the upper portion 6 of the sealed container 5, as close as possible, in the range of 90°–95° F., however temperature control in this area is not as critical as in the lower portion 7.

A second frame 28 is constructed around the lower portion 7 of the sealed container 5 spaced outwardly from the sealed container to leave a passageway 29 of sufficient size to walk in. A second layer of transparent material 30 such as clear plastic is attached to the first frame 24 around the upper side wall segment 6 of the sealed container 5 and to the second frame 28 around the lower portion 7 thereby protecting the enclosed materials from weather elements such as rain and wind, while allowing the solar radiation to be transmitted. The air trapped in the passageway 29 is heated by the solar radiation, thereby acting as a second insulative layer. The solar heated structure is illustrated in FIG. 4 showing the layers of heat absorptive insulative and transparent materials in the particular sequence disclosed.

When it is desired to heat the contents of the container during sunlight hours the panels of insulation 26 facing the sun are removed. The removed panels 31 are placed against the sealed container in an area not facing the sun as shown in FIG. 3, allowing the heat absorptive material 21 to absorb the energy associated with the solar radiation, which is transferred to the sealed container 5. As the position of the sun changes, or if it is no longer desirable to raise the temperature of the sealed container, the removed panels 31 are replaced to insulate the sealed container against heat lost to the outside environment. Additional panels 26 can be removed as the position of the sun or temperature of the sealed container permit. When the temperature outside the solar heated structure are in excess of 95° F., the panels 26 remain fastened to the sealed container to insulate it against the excess heat.

In addition to the solar heated structure 8, secondary gas heating means 9 are provided for use in heating the slurry in the lower portion 7 as may be required when outside temperatures are very low or during non-sunlight hours. Methane gas from the storage tank 12 is burned in the gas burner 32 to heat water. The heated water is circulated through coils 33 running through the slurry within the sealed container 5 thereby heating the slurry.

The embodiments of the invention in which an exclusive property or privilege is claimed are defined as follows:

1. A solar heated anaerobic digestor adapted to utilize a slurry of organic material capable of decomposing to produce a liquid fertilizer and methane gas, comprising:
    sealed digestor container means having adjoining upper and lower portions defined by upper and lower side wall segments, the lower portion of which is operative to contain the organic material and the upper portion of which is capable of containing the gas produced;

means, connected to and communicating with the sealed container means, for introducing the slurry into the container means;

means, connected to the container means and communicating with the lower portion, for draining slurry product from the container means;

means, connected to and communicating with the upper portion of the container means, for withdrawing gas produced;

means in the lower portion for stirring the slurry;

secondary heating means for heating the slurry present in the lower portion;

a layer of heat absorptive material wrapped around the lower side wall segment;

a plurality of abutting removable panels of insulative material enclosing the layer of heat absorptive material;

a layer of insulative material wrapped around the upper side wall segment of the container means;

a layer of transparent material wrapped around the panels and the upper side wall insulative material; said layer of transparent material being spaced outwardly from the insulating panels, whereby some of the panels may be temporarily removed to permit solar radiation to heat an exposed portion of the heat absorptive material, and may be replaced when the solar radiation diminishes, thereby enabling a combination of solar heat and heat obtained from the secondary heating means to be used to maintain the temperature of the contained slurry at a desirable level;

first frame means attached to the container for mounting the heat absorptive material and insulative material and insulative panels; and second frame means spaced outwardly from the lower side wall segment for mounting the transparent material around the lower side wall segment.

2. The solar heated anaerobic digestor as set forth in claim 1 wherein:

the means for draining the slurry comprises an effluent line extending from within the slurry to the exterior of the sealed container means in a manner such that pressure extending by the gas produced within the sealed container forces the slurry to drain from the container means; and the stirring means comprises gas bubbling means.

3. The solar heated anaerobic digestor as set forth in claim 2, which further comprises:

a layer of transparent material attached to the first frame means between the panels and the heat absorptive material covering the lower side wall segment operative to trap air between the heat absorptive material and the transparent material.

* * * * *